US00PP21861P2

(12) United States Plant Patent
Egger

(10) Patent No.: US PP21,861 P2
(45) Date of Patent: Apr. 5, 2011

(54) ***HEUCHERA* PLANT NAMED 'LIME MARMALADE'**

(50) Latin Name: ***Heuchera* hybrid**
Varietal Denomination: Lime Marmalade

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 36 days.

(21) Appl. No.: 12/653,632

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell

(74) *Attorney, Agent, or Firm* — Klarquist Sparkman, LLP

(57) ABSTRACT

A new and distinct *Heuchera* plant substantially as shown and described, characterized by ruffled, lime green leaves, large plant size, and excellent vigor.

1 Drawing Sheet

Botanical denomination: *Heuchera* hybrid.

Variety designation: 'Lime Marmalade'.

Cross Reference to: *Heuchera* 'Marmalade', U.S. Plant Pat. No. 15,945.

The present invention relates to a new and distinct cultivar of *Heuchera* and given the cultivar name of 'Lime Marmalade'. *Heuchera* is in the family Saxifragaceae. *Heuchera* 'Lime Marmalade' originated as a tissue culture mutation of *Heuchera* 'Marmalade', U.S. Plant Pat. No. 15,945. Compared to *Heuchera* 'Lime Rickey', U.S. Plant Pat. No. 16,210, the new cultivar grows larger, is more vigorous, and has taller flower stems. Compared to *Heuchera* 'Marmalade', the new cultivar had lime green foliage rather than amber.

This new *Heuchera* is distinguished by:

1. Lime colored, ruffled leaves,
2. large plant size,
3. and excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two year old *Heuchera* 'Lime Marmalade' in bloom, growing in a one gallon container in the shade house in late spring in Canby, Oreg.

FIG. 2 shows a one year old *Heuchera* 'Lime Marmalade' in a one gallon container grown outside all winter in early March in Canby, Oreg.

DETAILED PLANT DESCRIPTION

The following is a detailed description of the new *Heuchera* cultivar based on observations of a one-year-old specimen grown in a 1 gallon container in a cool greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 1999 edition.

Plant:

*Form.*—Basal rosette, herbaceous perennial.
*Hardiness.*—USDA Zone 4 to 9.
*Size.*—20 cm tall from top of the foliage to the ground and 35 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Basal.
*Shape.*—Ovate.
*Lobing/division.*—5 main lobes, with 2 to 3 shallow secondary lobes.
*Venation.*—Palmate.
*Margins.*—Crenate and undulate.
*Apex.*—Mucronulate.
*Base.*—Cordate, lobes overlapping at the base.
*Blade size.*—8.5 to 11.5 cm long and 7.5 to 10 cm wide.
*Surface texture.*—Sparsely glandular both sides.
*Texture.*—Thin, leathery.
*Petiole description.*—Grows to 11.5 cm long and 2 mm wide, glandular hairs, Greyed Purple 185B at the base to Yellow Green 145B below the blade.
*Leaf color.*—Spring, topside Yellow Green 145A, bottom side Yellow Green 145B; summer, fall, and winter topside, Yellow Green 144A, bottom side 146C.

Inflorescence:

*Size.*—Grows to 6 cm wide and 25 cm long.
*Type.*—Thyrse.
*Number of flowers per thyrse.*—80 to 120 per thyrse.
*Number of thyrse.*—6 in first spring bloom.
*Peduncle.*—About 55 cm tall, 3 to 4 mm wide at base, Greyed Brown 199A near base to Yellow Green 153A near tip, glandular hairs, with 2 to 4 petiolate leaves (ovate, blades grow to 7 cm long and 6 cm wide with a lobed and crenate margin, Yellow Green 145A).

*Pedicel.*—Variable in size, with glandular hairs, Yellow Green 153A.

*Bloom period.*—Late April to June in Canby, Oreg.

Flower bud:

*Size.*—2.5 mm wide and 4 mm long.

*Description.*—Glandular puberulent, ovoid, with extruding filaments.

*Color.*—Top half is White 155D with lime green tips Yellow Green 145A, bottom half is Yellow Green 145A.

Flower:

*Type.*—Perfect.

*Shape.*—Campanulate.

*Size.*—6 mm long and 5 mm wide.

*Petal description.*—5 in number, 2 mm long, spatulate with a clawed base, strongly reflexed, tip acute, margin entire, glabrous on top and glandular on bottom side, White 155D on both sides.

*Calyx description.*—3 mm long and 4 mm wide, with 5 lobes, divided ⅓ way to the base, glandular hairs on both sides, tip obtuse, margin entire, lobes White 155D with tips Yellow Green 145A, bottom ⅔ is Yellow Green 145A on both sides.

*Stamen description.*—5 in number, 2.5 mm long, filament 2 mm long, White 155D, anther 1 mm long, Orange 25A, pollen Orange Red 31A.

*Pistil description.*—One central two beaked pistil, 5 mm long, ovary 2 mm long and Yellow Green 145B, each style 3 mm long and White 155D.

*Fragrance.*—None.

*Lastingness.*—Each thyrse blooms for about 2 weeks on the plant.

Fruit:

*Type.*—Two beaked capsule.

*Size.*—7 mm deep by 2 mm wide.

*Fertility.*—Good.

*Color.*—Greyed Brown 199A.

Seed:

*Shape.*—Linear.

*Size.*—2 mm long.

*Color.*—Black, RHS 202A.

Disease and pest tolerance: No known resistance to rust, a common problem with light leaf type *Heuchera*. Excellent disease tolerance to powdery mildew. All *Heuchera* are susceptible to root weevils.

I claim:

1. A new and distinct *Heuchera* plant as herein illustrated and described.

* * * * *

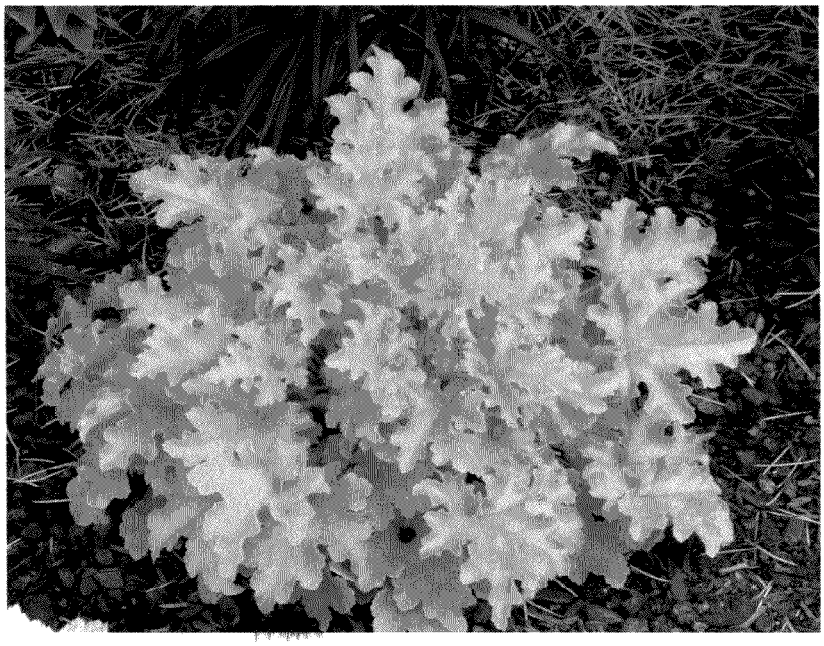

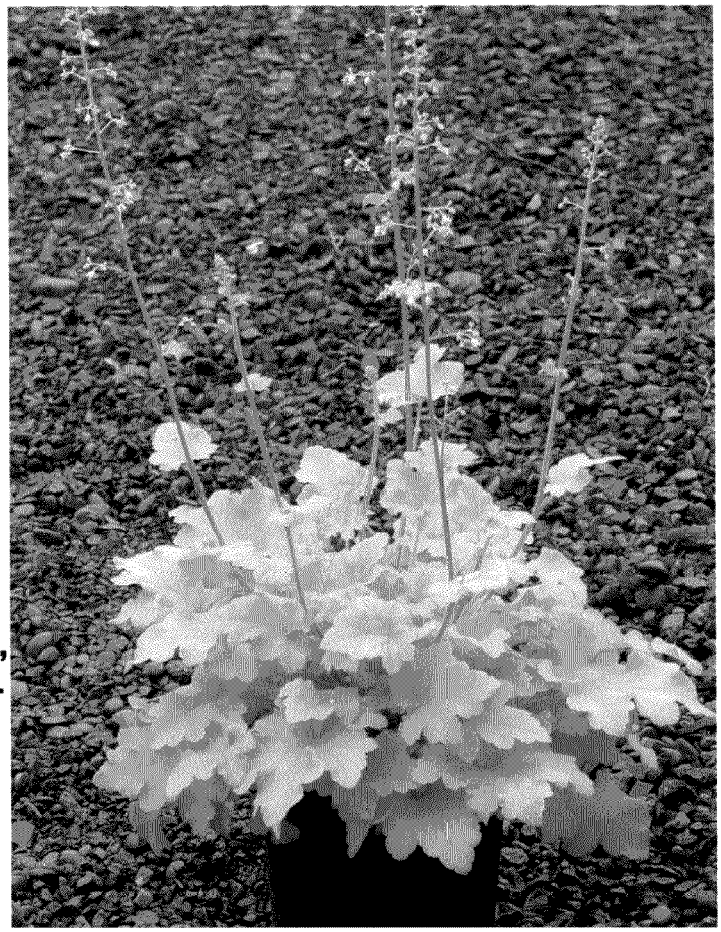
Figure 1 above,
Figure 2 below.